(12) United States Patent
Liu et al.

(10) Patent No.: US 11,401,495 B2
(45) Date of Patent: *Aug. 2, 2022

(54) POWER DEVICE OF A MICRO CHANNEL FOR EXTERNAL CIRCULATION OF A BIOREACTOR

(71) Applicant: ALIT BIOTECH (SHANGHAI) CO., LTD., Shanghai (CN)

(72) Inventors: Yu Liu, Shanghai (CN); Rui Chen, Shanghai (CN)

(73) Assignee: ALIT BIOTECH (SHANGHAI) CO., LTD., Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 17/478,879

(22) Filed: Sep. 18, 2021

(65) Prior Publication Data
US 2022/0186170 A1 Jun. 16, 2022

Related U.S. Application Data

(63) Continuation of application No. 17/198,295, filed on Mar. 11, 2021.

(30) Foreign Application Priority Data

Dec. 10, 2020 (CN) .......................... 202011437937.7

(51) Int. Cl.
C12M 3/00 (2006.01)
C12M 1/00 (2006.01)
C12M 1/26 (2006.01)

(52) U.S. Cl.
CPC ............ *C12M 33/12* (2013.01); *C12M 29/14* (2013.01); *C12M 29/16* (2013.01); *C12M 33/04* (2013.01); *C12M 33/14* (2013.01)

(58) Field of Classification Search
CPC ....... B01L 2300/123; B01L 2300/0867; B01L 2300/0887; B01L 2400/0638; B01L 2400/0478
See application file for complete search history.

(56) References Cited

U.S. PATENT DOCUMENTS 4,479,760 A * 10/1984 Bilstad ................ A61M 1/3496
128/DIG. 12
5,593,290 A * 1/1997 Greisch ................. F04B 43/021
417/478

(Continued)

FOREIGN PATENT DOCUMENTS

CN 101031500 A 9/2007
CN 205874406 U 1/2017

(Continued)

OTHER PUBLICATIONS

International Search Report in PCT/CN2021/133901 dated Mar. 1, 2022, 5 pages.

(Continued)

*Primary Examiner* — Nathan A Bowers
(74) *Attorney, Agent, or Firm* — Metis IP LLC (57) ABSTRACT

The present disclosure provides a power device of a micro channel for external circulation of a bioreactor. The power device of the micro channel may be disposed outside the bioreactor and in fluid connection with the bioreactor, the power device of the micro channel may be of a shape of a box body. The power device of the micro channel may comprise: a stacked layer disposed in the box body, including a first shell plate, a second shell plate, and a sealing film sandwiched between the first shell plate and the second shell plate; and a liquid buffer device including a first liquid cavity and a second liquid cavity disposed in the box body, the first liquid cavity and the second liquid cavity may be fixed to an outer end surface of the stacked layer. The power device of (Continued)

the micro channel may be of a box shape, thereby reducing the volume and production cost thereof.

20 Claims, 6 Drawing Sheets

(56) References Cited

U.S. PATENT DOCUMENTS

| | | | |
|---|---|---|---|
| 8,986,254 B2* | 3/2015 | Morris | A61M 1/14 604/153 |
| 9,845,794 B2* | 12/2017 | Seith | F04B 43/026 |
| 2005/0006310 A1 | 1/2005 | Agrawal et al. | |
| 2005/0260745 A1* | 11/2005 | Domansky | C12M 23/40 435/294.1 |
| 2006/0154341 A1* | 7/2006 | Chen | B01L 7/52 435/91.2 |
| 2006/0166357 A1* | 7/2006 | Takayama | F16K 99/0026 435/289.1 |
| 2007/0183935 A1* | 8/2007 | Clemmens | C12M 23/42 422/400 |
| 2009/0068700 A1* | 3/2009 | Wikswo | G01N 33/5005 435/29 |
| 2009/0215022 A1* | 8/2009 | Page | C12M 23/44 435/3 |
| 2012/0206547 A1 | 8/2012 | Shirotori | |
| 2013/0264286 A1 | 10/2013 | Tai | |
| 2014/0113366 A1 | 4/2014 | Dahan et al. | |
| 2019/0185803 A1 | 6/2019 | Grant | |
| 2020/0230597 A1* | 7/2020 | Lee | B01L 3/502715 |

FOREIGN PATENT DOCUMENTS

| | | |
|---|---|---|
| CN | 107782657 A | 3/2018 |
| CN | 206776732 U | 4/2019 |
| CN | 112553072 A | 3/2021 |
| JP | 2012166473 A | 9/2012 |

OTHER PUBLICATIONS

Written Opinion in PCT/CN2021/133901 dated Mar. 1, 2022, 5 pages.

* cited by examiner

POWER DEVICE OF A MICRO CHANNEL FOR EXTERNAL CIRCULATION OF A BIOREACTOR

CROSS-REFERENCE TO RELATED APPLICATIONS

This application is a continuation of U.S. patent application Ser. No. 17/198,295, filed Mar. 11, 2021, which claims priority of Chinese Patent Application No. 202011437937.7, filed on Dec. 10, 2020, the contents of which are hereby incorporated by reference.

TECHNICAL FIELD

The present disclosure generally relates to the field of bioreactors, and in particular, to a power device of a micro channel for external circulation of a bioreactor.

BACKGROUND

In a design of animal cell bioreactors, more and more processes involve circulation of cells outside the tank to renew the culture fluid, transfer oxygen, separate cell metabolites, or separate cells and culture fluid, or the like. Therefore, the application value of power components of the micro channel for the external circulation of the bioreactor tank is getting higher and higher.

Taking the separation of culture fluid and cells as an example, these processes may include perfusion culture, fluid exchange or cell cleaning. Traditional separation apparatuses include an alternating tangential flow filtration (ATF) system, a tangential flow filtration (TFF) system, etc. These systems use a centrifugal pump or a diaphragm pump to provide power and pump a mixture of cells and a culture fluid to a hollow fiber column, and use fiber pores of the hollow fiber column to separate cells and the culture fluid.

Some systems use a centrifugal pump to provide power for pumping the mixture of cells and the culture fluid. However, the centrifugal pump has a disadvantage of, for example, an excessive shear force. Animal cells (especially human T cells or stem cells) are very sensitive to the shear force. An excessive shear force may cause the oncogenesis of stem cells or loss of cell markers, thereby seriously affecting the safety of cell therapy products. Some systems use a diaphragm pump to provide power for pumping the mixture of cells and the culture fluid. However, the diaphragm pump has a disadvantage of, for example, nonlinear pressurization of liquid in the pipeline. Non-linear pressurization can lead to a relatively large fluctuation of an instantaneous pressure in a culture system, thereby introducing one or more potential effects on the stability of the process.

An injection pump that drives a gas to drive liquid circulation has been developed. The injection pump effectively solves the problem of an excessive shear force, and reduces the influence of the nonlinear pressure change of the liquid in the flexible diaphragm pump pipeline. However, in actual use of bioreactors, the injection pump and valves may be disposed separately from each other. These components are not only large in size and high in price, but also large in quantity and high in assembly requirements. In addition, multiple pipelines are used to connect the injection pump, valves and other units to the bioreactor, which is inconvenient to operate.

SUMMARY

According to an aspect of the present disclosure, a power device of a micro channel that can overcome at least one defect in the prior art is provided.

The subject technology of the present disclosure is explained in terms of various aspects described below. For convenience, various examples of various aspects of the subject technology are described as labeled terms (1, 2, 3, etc.). These terms are provided as examples, rather than limiting the subject technology of this disclosure.

In one aspect of the present disclosure, a power device of a micro channel for external circulation of a bioreactor is provided. The power device of the micro channel may be disposed outside the bioreactor and in fluid connection with the bioreactor, the power device of the micro channel may be of a shape of a box body, the power device of the micro channel may comprise:

a stacked layer disposed in the box body, including a first shell plate, a second shell plate, and a sealing film sandwiched between the first shell plate and the second shell plate; and a liquid buffer device including a first liquid cavity and a second liquid cavity disposed in the box body, the first liquid cavity and the second liquid cavity being fixed to an outer end surface of the stacked layer;

wherein a first liquid channel, a second liquid channel, a third liquid channel, and a fourth liquid channel may be recessed from an inner surface of the first shell plate; a top of the liquid channel, a top of the second liquid channel, a top of the third liquid channel, and a top of the fourth liquid channel may be covered and sealed by the sealing film; the first liquid cavity and the second liquid cavity may be in fluid connection with a functional device located downstream of the power device of the micro channel, respectively, via the first liquid channel and the second liquid channel; the first liquid cavity and the second liquid cavity may be in fluid connection with the bioreactor, respectively, via the third liquid channel and the fourth liquid channel;

the first liquid channel, the second liquid channel, the third liquid channel, and the fourth liquid channel may be equipped with a first valve, a second valve, a third valve, and a fourth valve, respectively; each of the first valve, the second valve, the third valve, and the fourth valve may include a valve body cavity and a spool cavity that are in fluid communication with each other; and the valve body cavities may be recessed from an inner surface of the first shell plate, and tops of the valve body cavities may be covered and sealed by the sealing film.

In some embodiments, the power device of the micro channel may further include a power unit fixed to the box body, and the first liquid cavity and the second liquid cavity may be in gas communication with the power unit.

In some embodiments, the power unit may include a syringe pump or an air cylinder.

In some embodiments, a volume of each of the first liquid cavity and the second liquid cavity may be 0.01-0.8 bioreactor culture volume.

In some embodiments, a pressure sensor may be installed in at least one of the first liquid channel and the second liquid channel to monitor a clogging state of the downstream functional device.

In some embodiments, at least one of the first liquid channel, the second liquid channel, the third liquid channel, or the fourth liquid channel may be configured on the first shell plate through at least one of machining, laser etching, or soft plastic injection molding.

In some embodiments, a cross section perpendicular to the first shell plate of at least one of the first liquid channel, the second liquid channel, the third liquid channel, or the fourth liquid channel may be semicircular or rectangular, and a diameter or a side length of the at least one of the first liquid channel, the second liquid channel, the third liquid channel, or the fourth liquid channel may be in a range from 0.01 mm to 2 mm.

In some embodiments, the diameter or the side length of the at least one of the first liquid channel, the second liquid channel, the third liquid channel, or the fourth liquid channel may be in a range from 0.1 mm to 1 mm.

In some embodiments, the valve body cavities of the first valve, the second valve, the third valve and the fourth valve may be located in the first liquid channel, the second liquid channel, the third liquid channel, and the fourth liquid channel, respectively.

In some embodiments, a cross section of the valve body cavities perpendicular to the first shell plate may be larger than a cross section of a corresponding liquid channel.

In some embodiments, a cross section of the valve body cavities perpendicular to the first shell plate may be circular, elliptical, square, or rectangular.

In some embodiments, the valve body cavities may be configured on the first shell plate through at least one of machining, laser etching, or soft plastic injection molding.

In some embodiments, the spool cavities may be configured as through cavities provided on the second shell plate, and positions of the spool cavities may correspond to positions of the valve body cavities.

In some embodiments, the power device of the micro channel may further include an additional power unit fixed to the box body, and the spool cavities may be in fluid communication with the additional power unit.

In some embodiments, the power device of the micro channel may further comprise an additional power unit fixed to the box body, and the spool cavities may be in fluid communication with the additional power device.

In some embodiments, the additional power unit may be configured to push a gas into at least one of the spool cavities to generate a positive pressure in the at least one of the spool cavities, so that the sealing film seals the at least one of the valve body cavities to close a corresponding liquid channel, and may further be configured to suction the gas out from the at least one of the spool cavities to generate a negative pressure in the at least one of the spool cavities, so that the sealing film releases the at least one of the valve body cavities to open the corresponding liquid channel.

In some embodiments, the downstream functional device may include at least one of a cell filtration device, a gas exchange device, or a dialysis device.

In some embodiments, the cell filtration device may include a hollow fiber column.

In some embodiments, a length of the box body may be in a range from 1 cm to 8 cm, a width of the box body may be in a range from 1 cm to 15 cm, and a height of the box body may be in a range from 1 cm to 15 cm.

In some embodiments, the first liquid cavity and the second liquid cavity may be configured such that when the third valve is opened and the first valve is closed, a gas may be suctioned out from the first liquid cavity, and the liquid in the bioreactor may be suctioned into the first liquid cavity through the third liquid channel, the fourth valve may be closed, the second valve may be opened, and the gas may be pushed into the second liquid cavity, the liquid in the second liquid cavity may leave the second liquid cavity and may be pushed to the downstream functional device through the second liquid channel.

In some embodiment, the first liquid cavity and the second liquid cavity may be configured such that when the third valve is closed and the first valve is opened, a gas may be pushed into the first liquid cavity, and the liquid in the first liquid cavity may leave the first liquid cavity and may be pushed into the downstream functional device through the first liquid channel, the fourth valve may be opened, the second valve may be closed, the gas may be suctioned out from the second liquid cavity, and the liquid in the bioreactor may be suctioned into the second liquid cavity through the fourth liquid channel.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

It should be understood that the foregoing general description and the following detailed description are both exemplary and illustrative, and are intended to provide a further description of the subject technology of the claimed disclosure.

BRIEF DESCRIPTION OF THE DRAWINGS

Based on the following specific embodiments and the drawings, various aspects of the present disclosure will be better understood. In the drawings.

DETAILED DESCRIPTION

The present disclosure will be described below with reference to the accompanying drawings, in which the drawings illustrate several embodiments of the present disclosure. However, it should be understood that the present disclosure can be presented in many different ways, and is not limited to the embodiments described below. In fact, the embodiments described below are intended to make the disclosure of the present disclosure more complete and fully explain the protection scope of the present disclosure to those skilled in the art. It should also be understood that the embodiments disclosed herein can be combined in various ways to provide more additional embodiments.

It should be understood that in all the drawings, the same reference numerals denote the same elements. In the drawings, the dimensions of certain features may be deformed for clarity.

It should be understood that the terms in the specification are only used to describe specific embodiments and are not intended to limit the present disclosure. Unless otherwise defined, all terms (including technical terms and scientific terms) used in the specification have the meanings commonly understood by those skilled in the art. For brevity and/or clarity, well-known functions or structures may not be described in detail.

The singular forms "a", "the" and "is" used in the specification include plural forms unless clearly indicated. The terms "including", "comprising" and "containing" used in the specification indicate the presence of the claimed feature, but do not exclude the presence of one or more other features. The term "and/or" used in the specification includes any and all combinations of one or more of the related listed items. The terms "between X and Y" and "between about X and Y" used in the specification should be interpreted as including X and Y. The term "between about X and Y" used in this specification means "between about X and about Y", and the term "from about X to Y" used in this specification means "from about X to about Y".

In the specification, when an element is referred to as being "on", "attached" to another element, "connected" to another element, "coupled" to another element, or "contacting" another element, etc., the element may be directly on another element, attached to another element, connected to another element, coupled to another element, or contacting another element, or an intermediate element may be present. In contrast, it is said that an element is "directly on" another element, "directly attached" to another element, "directly connected" to another element, "directly coupled" to another element, or "directly contacting" another element, there will be no intermediate element. In the specification, when an element is arranged "adjacent" to another element, it may mean that the element has a portion overlapping with an adjacent element or a portion located above or below the adjacent element.

In the specification, terms such as "upper", "lower", "left", "right", "front", "rear", "high", "low", etc. can describe the relation of one element and another element in the drawings. It should be understood that, in addition to the orientation shown in the drawings, the terms describing spatial relationship also indicate different orientations of the device in use or operation. For example, when the device in the drawings is turned upside down, elements that were originally described as being "below" other elements may now be described as being "above" other elements. The device can also be oriented in other ways (e.g., rotated by 90 degrees or in other orientations), and the relative spatial relationship will be explained accordingly.

Figure 1:
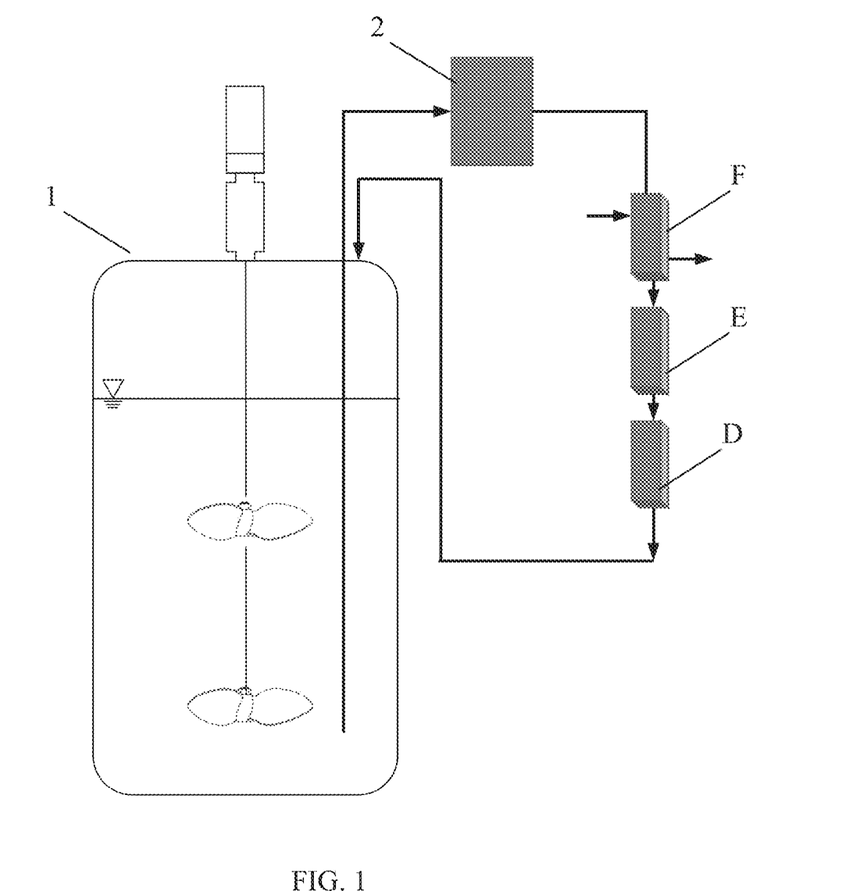
FIG. 1 is a schematic diagram illustrating a disposable power device of a micro channel.

FIG. 1 is a schematic diagram illustrating a disposable power device 2 of a micro channel according to a first embodiment of the present disclosure. The power device 2 of the micro channel may be in fluid connection with the bioreactor 1, and configured for cell circulation outside a tank of the bioreactor to facilitate downstream devices to perform cell filtration (see block F), gas exchange (see block E), dialysis (see block D), and other functions (the sequence of these functions can be arbitrary).

Figure 2A:
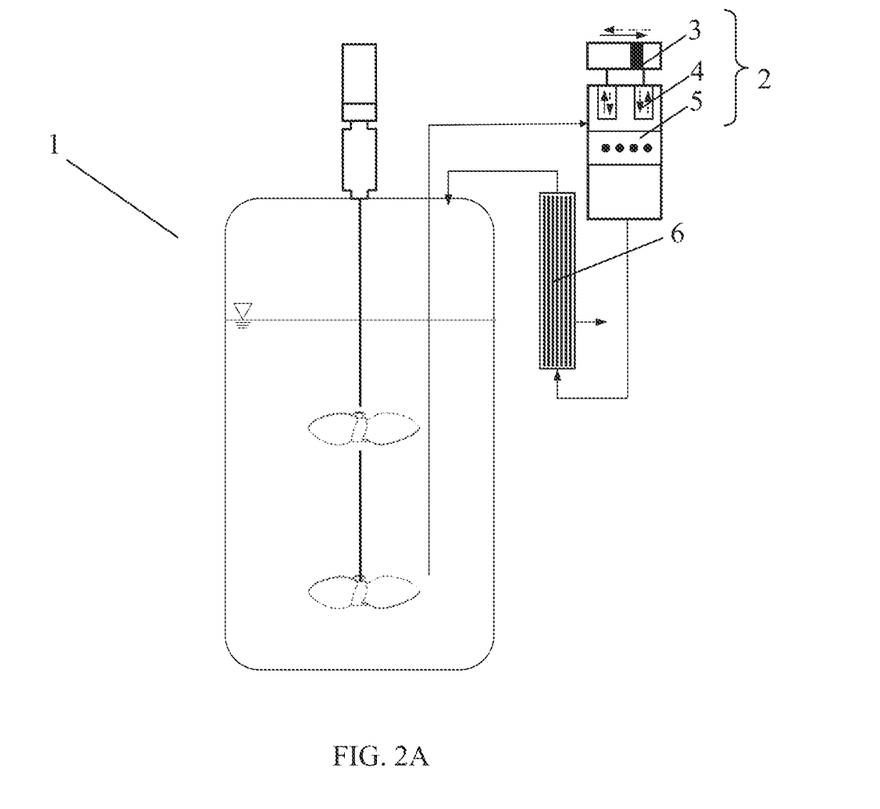
FIGS. 2A and 2B show a schematic diagram and a three-dimensional diagram illustrating an usage of the disposable power device of the micro channel according to some embodiments of the present disclosure.
Figure 2B:
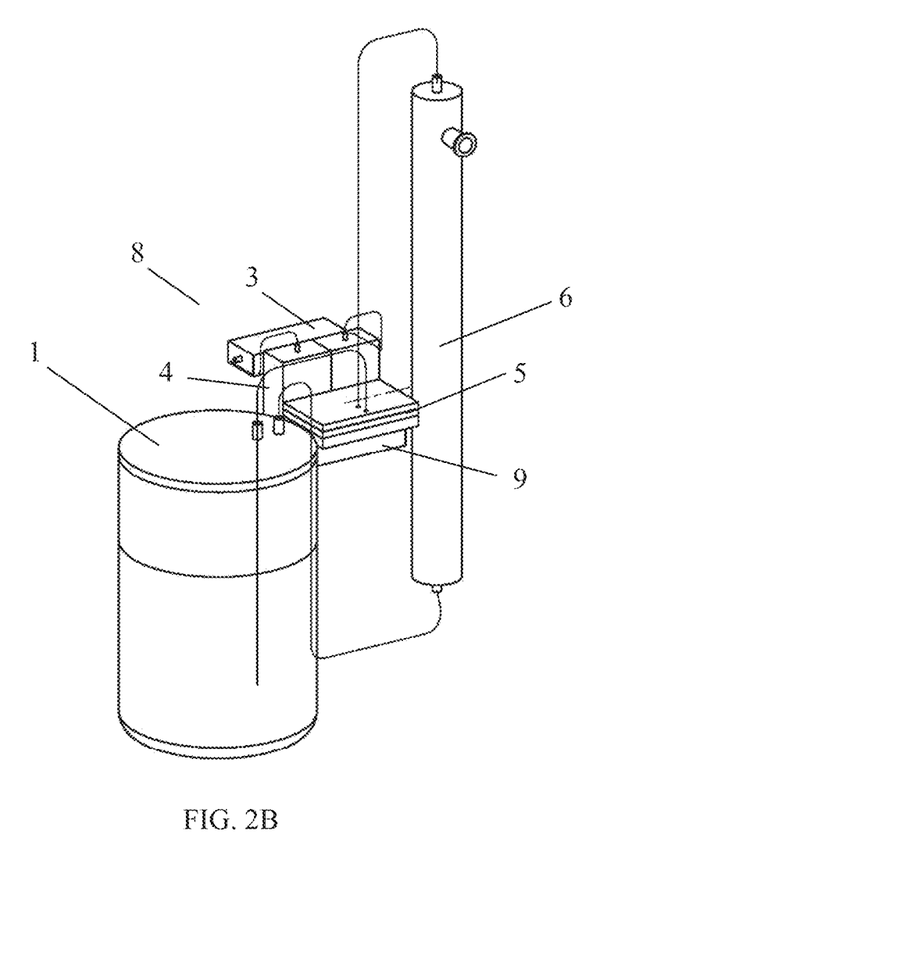
Figure 3A:
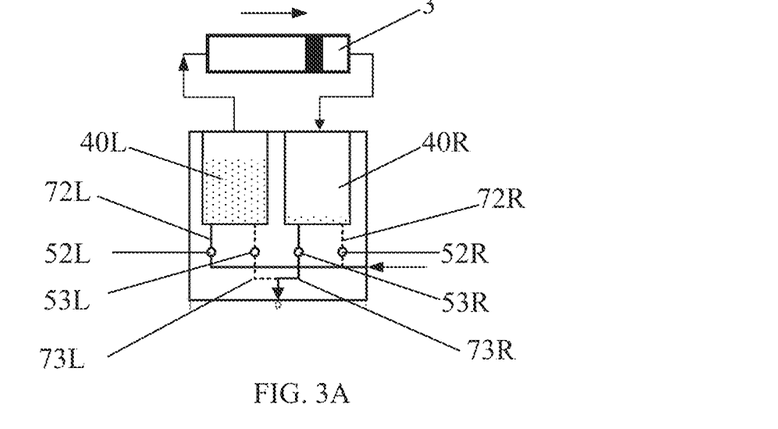
FIGS. 3A and 3B are schematic diagrams illustrating connections of components of the disposable power device of the micro channel shown in FIGS. 2A and 2B.
Figure 3B:
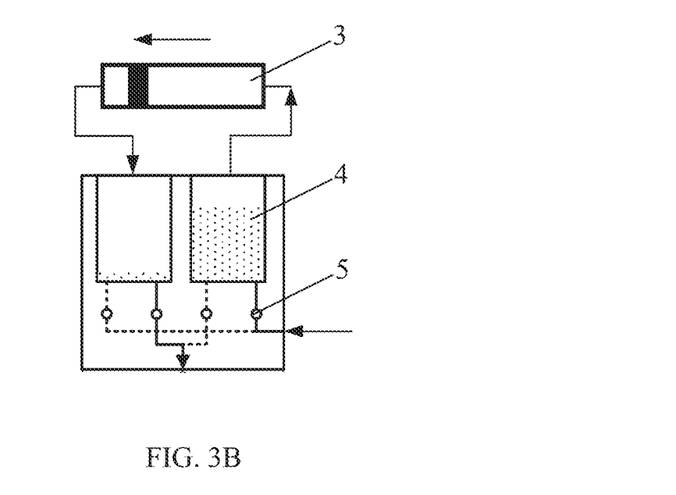
Figure 4:
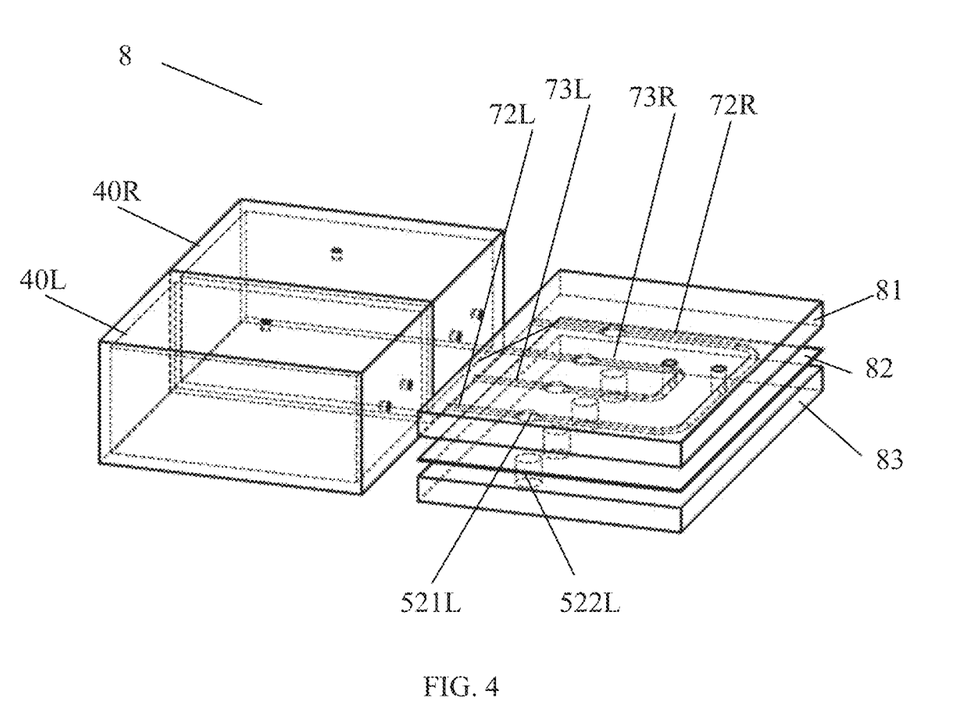
FIG. 4 shows an exploded perspective view illustrating the disposable power device of the micro channel without the relevant power unit.
Figure 5A:
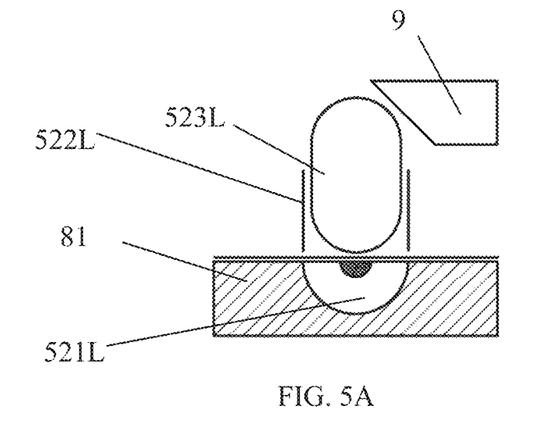
FIGS. 5A and 5B are schematic diagrams illustrating an example of the valve device of the disposable power device of the micro channel shown in FIGS. 2A and 2B.
Figure 5B:
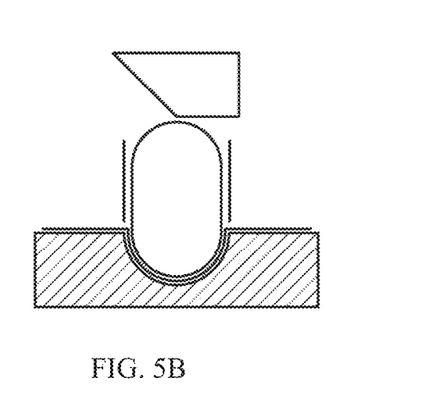
Figure 6A:
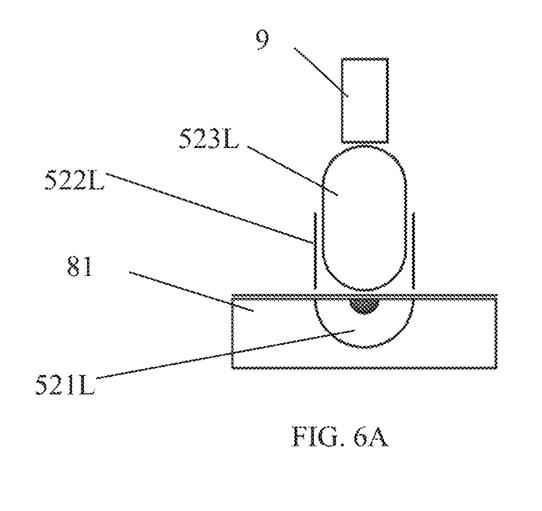
FIGS. 6A and 6B are schematic diagrams illustrating another example of the valve device of the disposable power device of the micro channel shown in FIGS. 2A and 2B.
Figure 6B:
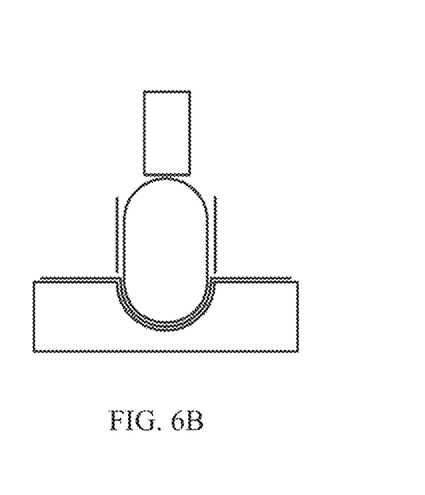

FIGS. 2A and 2B show a schematic diagram and a three-dimensional diagram illustrating an usage of the disposable power device 2 of the micro channel, FIGS. 3A and 3B are schematic diagrams illustrating connections of components of the disposable power device 2 of the micro channel, and FIG. 4 shows an exploded perspective view illustrating the disposable power device of the micro channel without the relevant power unit. As shown in the figure, the power device 2 of the micro channel may include a power unit 3, a liquid buffer device 4 and a valve device 5. The liquid buffer device 4 and the bioreactor 1, the valve device 5 and downstream functional devices (such as the cell filter device 6, or gas exchange device, dialysis device, etc.), and the liquid buffer device 4 and the valve device 5 may be in fluid connection through one or more liquid pipelines, respectively. The power unit 3 and the liquid buffer device 4 may be in fluid connection through one or more gas pipelines. The power unit 3 may be configured to drive the liquid to leave the bioreactor 1, and pass the liquid buffer device 4, the valve device 5 and one or more downstream functional devices, and finally be discharged. The liquid buffer device 4 may be configured to temporarily receive the liquid leaving the bioreactor 1, so that the liquid in the entire flow path flows smoothly without generating back and forth pressure fluctuations. The valve device 5 may be configured to control the opening and closing of the liquid pipeline(s).

The liquid buffer device 4 and the valve device 5 may be integrated into the box body 8 and arranged from a first end of the box body 8 to an opposite second end. The liquid buffer device 4 and the valve device 5 may be connected by a liquid pipeline disposed in the box body 8. The power unit 3 may be fixed to the first end of the box body 8 by various known methods (such as screw connection, welding, shape fitting, etc.), and in fluid connection with the liquid buffer device 4. The length of the box body 8 from the first end to the second end may be in a range from 1 cm to 8 cm, the width may be in a range from 1 cm to 15 cm, and the height may be in a range from 1 cm to 15 cm.

The liquid buffer device 4 may include two side-by-side liquid cavities 40L and 40R disposed near the first end of the box body 8. Each of the liquid cavities 40L and 40R may receive liquid inside the liquid cavity. In some embodiments, each of the liquid cavities 40L and 40R may be of a rectangular parallelepiped or a cube shape, and include an inner wall facing the valve device 5, an opposite outer wall, and a side wall connecting the inner wall and the outer wall. The liquid cavity 40L may include air holes disposed on the side wall or the outer wall, and a liquid inlet and a liquid outlet disposed on the inner wall. The air holes may be in fluid communication with the power unit 3, the liquid inlet may be in fluid communication with the bioreactor 1 through a liquid channel 72L disposed on the box body 8 and a separate liquid conduit (not shown). The liquid outlet may be in fluid communication with the downstream functional device(s) through a liquid channel 73L disposed on the box body 8.

The power unit 3 may be a device capable of driving a gas to reciprocate, including, for example, a syringe pump, an air cylinder, or the like. The gas (for example, the air) may exist between the power unit 3 and the liquid surface in the liquid cavity 40L. The power unit 3 may pump the gas out from the liquid cavity 40L through the air holes of the liquid cavity 40L, and generate a negative pressure in the liquid cavity 40L, thereby pumping the liquid in the bioreactor 1 into the liquid cavity 40L through the separate liquid conduit, the liquid channel 72L and the liquid inlet. The power unit 3 may further push the gas into the liquid cavity 40L through the air holes of the liquid cavity 40L, and generate a positive pressure in the liquid cavity 40L, thereby pushing the liquid in the liquid cavity 40L to the downstream functional device(s) through the liquid outlet and the liquid channel 73L. The power unit 3 may use the gas to generate a driving force and a draining force, thereby greatly reducing the damage to cells caused by other methods (such as peristaltic pumps or centrifugal pumps). Studies have shown that if the peristaltic pump circulates for more than 30 hours, the cell viability may decrease significantly.

The structure and function of the liquid cavity 40R may be substantially the same as or similar to those of the liquid cavity 40L, and correspondingly, the liquid cavity 40R may include one or more air holes, a liquid inlet and a liquid outlet. The air hole(s) may be in fluid communication with the power unit 3, the liquid inlet may be in fluid communication with the bioreactor 1 through a liquid channel 72R and a separate liquid conduit (not shown) disposed on the box body 8, and the liquid outlet may be in fluid communication with the downstream functional device(s) through a liquid channel 73R disposed on the box body 8. Similarly, the power unit 3 may push the liquid of the bioreactor 1 into and out of the liquid cavity 40R using a gas.

The volumes of the liquid cavities 40L and 40R may be determined based on a flow rate of the filter device 6, and may generally be 0.01-0.8 bioreactors culture volume. Maximum liquid volume in the liquid cavities 40L and 40R may account for 40%-80% of the volume of the liquid cavity to ensure a certain buffering and prevent the liquid from contacting the downstream functional device(s) when the liquid is suctioned. In some embodiments, one or more liquid level sensors may be installed in the liquid cavities 40L and 40R to determine the action time of the positive pressure and the negative pressure.

In addition to the liquid cavity 40L and the liquid cavity 40R, the box body 8 may further include a first shell plate 81, a sealing film 82, and a second shell plate 83 that stack on each other, and the sealing film 82 may be sandwiched between the first shell plate 81 and the second shell plate 83. The liquid channels 72L, 73L, 72R, 73R and the valve device 5 may be disposed between the stacked layer. The liquid cavities 40L and 40R may be fixed to an outer end surface of the stacked layer in various ways (for example, ultrasonic welding, bonding, etc.).

The liquid channels 72L, 73L, 72R, and 73R may be configured as micro channels, and may be recessed from an inner surface of the first shell plate 81, and a top of the liquid channels 72L, 73L, 72R, and 73R may be covered and sealed by the sealing film 82. The inlets of the liquid channels 72L and 72R may be exposed on a side wall of the box body 8, or configured as through holes on the second shell plate 83, and in fluid communication with the bioreactor 1 through one or more liquid conduits, and the outlets of the liquid channels 72L, 73L, 72R, and 73R may be respectively aligned and connected to the liquid inlet of the liquid cavity 40L and the liquid outlet of the liquid cavity 40R. The inlets of the liquid channels 73L and 73R may be respectively aligned and connected to the outlet of the liquid cavity 40L and the outlet of the liquid cavity 40R, and the outlets of the liquid channels 73L and 73R may be exposed on the side wall of the box body 8 or configured as through holes on a second shell plate 83. In some embodiments, the liquid channels 72L, 73L, 72R, and 73R may be configured on the first shell plate 81 by machining, laser etching, soft rubber injection molding, or the like. In some embodiments, a cross section (that is perpendicular to the first shell plate 81) of the liquid channels 72L, 73L, 72R, 73R may be of a shape of a semicircle or rectangle, and a diameter or side length of the liquid channels may be in a range from 0.01 mm to 2 mm, and more particularly from 0.1 mm to 1 mm. In some embodiments, one or more pressure sensors may be installed in the liquid channels 72L, 73L, 72R, and 73R to monitor whether the downstream functional device(s) are clogged.

The valve device 5 may be configured to control the opening and closing of the liquid channels. As shown in the figure, for the liquid cavity 40L, the valve device 5 may include an inlet valve 52L disposed in the liquid channel 72L, and an outlet valve 53L disposed in the liquid channel 73L. When the power unit 3 suctions the gas out from the liquid cavity 40L, the inlet valve 52L may be opened and the outlet valve 53L may be closed, so that the liquid in the bioreactor 1 is suctioned into the liquid cavity 40L through the liquid channel 72L. When the power unit 3 pushes the gas into the liquid cavity 40L, the inlet valve 52L may be closed and the outlet valve 53L may be opened, so that the liquid in the liquid cavity 40L is pushed to the downstream functional device(s) through the liquid channel 73L.

Similarly, for the liquid cavity 40R, the valve device 5 may include an inlet valve 52R disposed in the liquid channel 72R, and an outlet valve 53R disposed in the liquid channel 73R. When the power unit 3 suctions the gas out from the liquid cavity 40R, the inlet valve 52R may be opened and the outlet valve 53R may be closed, so that the liquid in the bioreactor 1 is suctioned into the liquid cavity 40R through the liquid channel 72R. When the power unit 3 pushes the gas into the liquid cavity 40R, the inlet valve 52R may be closed and the outlet valve 53R may be opened, so that the liquid in the liquid cavity 40R is pushed to the downstream functional device(s) through the liquid channel 73R.

The structures of the inlet valve 52L, the outlet valve 53L, the inlet valve 52R and the outlet valve 53R may be substantially the same or similar. In the following descriptions, the inlet valve 52L is taken as an example to illustrate the structure of the valve, but it should be understood that the same or similar structure is also applicable to the outlet valve 53L, the inlet valve 52R, and the outlet valve 53R. The inlet valve 52L may include a valve body cavity 521L and a spool cavity 522L. The valve body cavity 521L may be disposed in the liquid channel 72L. Similar to the structure of the liquid channel 72L, the valve body cavity 521L may be recessed from an inner surface of the first shell plate 81, and a top of the valve body cavity 521L may be covered and sealed by the sealing film 82. In some embodiments, a cross section of the valve body cavity 521L perpendicular to the first shell plate 81 may be larger than a cross section of the liquid channel 72L. The cross section of the valve body cavity 521L along a direction perpendicular to the first shell plate 81 may be of a circular, oval, square, rectangular, or any suitable shape. In some embodiments, the valve body cavity 521L may be configured on the first shell plate 81 by machining, laser etching, soft rubber injection molding, or the like. The spool cavity 522L may be a through cavity disposed on the second shell plate 83, and the position of the spool cavity 522L may correspond to the valve body cavity 521L. The power unit 9 (for example, an air cylinder, etc.) may be in fluid communication with the spool cavity 522L. The power unit 9 may push gas into the spool cavity 522L, and generate a positive pressure in the spool cavity 522L, thereby pushing the sealing film 82 to seal the valve body cavity 521L and close the liquid channel 72L. The power unit 9 may further suction the gas out from the spool cavity 522L, and generate a negative pressure in the spool cavity 522L, thereby causing the sealing film 82 to release the valve body cavity 521L to open the liquid channel 72L. The power unit 9 may be fixed to the box body 8 (for example, the second shell plate 83 of the box body 8) by various known methods (such as screw connection, welding, shape matching, etc.).

In some embodiments, as shown in FIGS. 5A and 5B, and FIGS. 6A and 6B, a spool 523L may be disposed in the spool cavity 522L, and may be driven by the power unit 9 to reciprocate into and out of the valve body cavity 521L. The spool 523L may be of a substantially cylindrical shape or a capsule shape. When the spool 523L enters the valve body cavity 521L, the valve body cavity 521L may be closed to close the liquid channel 72L; when the spool 523L leaves the valve body cavity 521L, the valve body cavity 521L may be released to open the liquid channel 72L.

Referring back to FIGS. 3A to 4, the downstream functional devices (such as the cell filtration device 6, the gas exchange device, the dialysis device, etc.) may be connected to the outlets (that is, outlets exposed on the side wall of the box body, or holes on the second shell plate 83) of the liquid channels 73L and 73R through fluid conduits to perform cell filtration, gas exchange, and/or dialysis. The cell filtration device 6 may be, for example, a hollow fiber column, or the like, and the liquid may pass through the fiber pores of the hollow fiber column to separate the culture solution and the cells.

The operation process of the disposable power device 2 of the micro channel according to an embodiment of the present disclosure will be described below. In some embodiments, the flow of the liquid may be reciprocating, i.e., the outflow of the liquid in the bioreactor 1 and the inflow of the liquid to the bioreactor 1 may be conducted by two pipelines, and the liquid in each pipeline may flow in one direction. First, as shown in FIG. 3A, the inlet valve 52L may be opened and the outlet valve 53L may be closed. The power unit 3 may suction the gas out from the liquid cavity 40L, and thus, the liquid in the bioreactor 1 may be suctioned to the liquid cavity 40L. After the liquid reaches a preset scale of the liquid cavity 40L, the inlet valve 52L may be closed and the outlet valve 53L may be opened. As shown in FIG. 3B, the power unit 3 may reverse and use a positive pressure to push the liquid out from the liquid cavity 40L, and push the liquid to the downstream functional device(s) (such as the cell filter device 6, or the gas exchange device or the dialysis device, etc.) through the liquid channel 73L to perform corresponding processing. Finally, the processed liquid may be discharged through the return conduit.

The operating states of the inlet valve 52R and the outlet valve 53R on the side of the liquid cavity 40R may be exactly opposite to those of the inlet valve 52L and the outlet valve 53L on the side of the liquid cavity 40L. As shown in FIG. 3A, when the power unit 3 suctions the liquid into the liquid cavity 40L based on a negative pressure, the inlet valve 52R may be closed and the outlet valve 53R may be opened. The power unit 3 may use a positive pressure to push the liquid out from the liquid cavity 40R, and reach the downstream functional device(s) (for example, the cell filtration device 6, or the gas exchange device, the dialysis device, etc.) through the liquid channel 73R for corresponding processing. Finally, the processed liquid may be discharged through the return conduit. As shown in FIG. 3B, when the power unit 3 uses a positive pressure to push the liquid out from the liquid cavity 40L, the inlet valve 52R may be opened and the outlet valve 53R may be closed and the power unit 3 may use a negative pressure to suction the gas out from the liquid cavity 40R, and thus, the liquid in the bioreactor 1 may be suctioned into the liquid cavity 40R by using a negative pressure.

The liquid cavities 40L and 40R may cooperate with each other, repeatedly and periodically, so that the liquid can be continuously pumped from the bioreactor 1 to the downstream functional device(s). Compared with the reciprocating movement of a single liquid cavity, the using of the two liquid cavities may make the flow in the entire pipeline smooth without generating back and forth pressure fluctuations.

Compared with a traditional power device of the micro channel, the power device of the micro channel according to the embodiments of the present disclosure may be of a box shape, thereby reducing the volume and production cost thereof.

The power device of the micro channel according to the embodiment of the present disclosure may use a gas as a driving power and/or a suction power of the liquid, thereby greatly reducing the damage to cells caused by other methods (such as peristaltic pumps or centrifugal pumps).

The power device of the micro channel according to the embodiment of the present disclosure may reduce the complexity and error-prone nature (of the traditional power device of the micro channel) caused by the valve(s) and pipeline connection(s), thereby improving the stability of the system.

A micro channel switch may be integrated into the power device of the micro channel according to the embodiments of the present disclosure, and the opening and closing of the micro channel switch may be controlled by a membrane. The switching between the logic of the power system and the multi-channels may be conveniently controlled, thereby making the system flexible.

Although exemplary embodiments of the present disclosure have been described, those skilled in the art should understand that various changes and alternations can be made to the exemplary embodiments of the present disclosure without substantially departing from the spirit and scope of the present disclosure. Therefore, all changes and alternations are included in the protection scope of the present disclosure defined by the claims. The present disclosure is defined by the appended claims, and equivalents of these claims are also included.

We claim:

1. A pumping device of a micro channel for external circulation of a bioreactor, the pumping device of the micro channel being in fluid connection with the bioreactor, the pumping device of the micro channel being of a shape of a box body, the pumping device of the micro channel comprising:
   a stacked layer disposed in the box body, including a first shell plate, a second shell plate, and a sealing film sandwiched between the first shell plate and the second shell plate; and
   a liquid buffer device including a first liquid cavity and a second liquid cavity disposed in the box body; wherein
      a first liquid channel, a second liquid channel, a third liquid channel, and a fourth liquid channel are recessed from an inner surface of the first shell plate;
      a top of the first liquid channel, a top of the second liquid channel, a top of the third liquid channel, and a top of the fourth liquid channel are covered and sealed by the sealing film;
      the first liquid cavity and the second liquid cavity are in fluid connection with a functional device located downstream of the pumping device of the micro channel, respectively, via the first liquid channel and the second liquid channel;

the first liquid cavity and the second liquid cavity are in fluid connection with the bioreactor, respectively, via the third liquid channel and the fourth liquid channel;

the first liquid channel, the second liquid channel, the third liquid channel, and the fourth liquid channel are equipped with a first valve, a second valve, a third valve, and a fourth valve, respectively; and each of the first valve, the second valve, the third valve, and the fourth valve includes a valve body cavity and a piston cavity that are in fluid communication with each other.

2. The pumping device of the micro channel of claim 1, wherein the pumping device of the micro channel further comprises a pumping unit fixed to the box body, and the first liquid cavity and the second liquid cavity are in gas communication with the pumping device.

3. The pumping device of the micro channel of claim 2, wherein the pumping unit includes a syringe pump or an air cylinder.

4. The pumping device of the micro channel of claim 1, wherein a volume of each of the first liquid cavity and the second liquid cavity is 0.01-0.8 bioreactor culture volume.

5. The pumping device of the micro channel of claim 1, wherein a pressure sensor is installed in at least one of the first liquid channel and the second liquid channel to monitor a clogging state of the downstream functional device.

6. The pumping device of the micro channel of claim 1, wherein at least one of the first liquid channel, the second liquid channel, the third liquid channel, or the fourth liquid channel is configured on the first shell plate through at least one of machining, laser etching, or soft plastic injection molding.

7. The pumping device of the micro channel of claim 1, wherein a cross section perpendicular to the first shell plate of at least one of the first liquid channel, the second liquid channel, the third liquid channel, or the fourth liquid channel is semicircular or rectangular, and a diameter or a side length of the at least one of the first liquid channel, the second liquid channel, the third liquid channel, or the fourth liquid channel is in a range from 0.01 mm to 2 mm.

8. The pumping device of the micro channel of claim 7, wherein the diameter or the side length of the at least one of the first liquid channel, the second liquid channel, the third liquid channel, or the fourth liquid channel is in a range from 0.1 mm to 1 mm.

9. The pumping device of the micro channel of claim 1, wherein the valve body cavities of the first valve, the second valve, the third valve and the fourth valve are located in the first liquid channel, the second liquid channel, the third liquid channel, and the fourth liquid channel, respectively.

10. The pumping device of the micro channel of claim 9, wherein a cross section of the valve body cavities perpendicular to the first shell plate is larger than a cross section of a corresponding liquid channel.

11. The pumping device of the micro channel of claim 9, wherein a cross section of the valve body cavities perpendicular to the first shell plate is circular, elliptical, square, or rectangular.

12. The pumping device of the micro channel of claim 9, wherein the valve body cavities are configured on the first shell plate through at least one of machining, laser etching, or soft plastic injection molding.

13. The pumping device of the micro channel of claim 9, wherein the piston cavities are configured as through cavities provided on the second shell plate, and positions of the piston cavities correspond to positions of the valve body cavities.

14. The pumping device of the micro channel of claim 9, further comprises an additional pumping unit fixed to the box body, and the piston cavities are in fluid communication with the additional pumping unit.

15. The pumping device of the micro channel of claim 14, wherein the additional pumping unit is configured to push a gas into at least one of the piston cavities to generate a positive pressure in the at least one of the piston cavities, so that the sealing film seals the at least one of the valve body cavities to close a corresponding liquid channel, and is further configured to suction the gas out from the at least one of the piston cavities to generate a negative pressure in the at least one of the piston cavities, so that the sealing film releases the at least one of the valve body cavities to open the corresponding liquid channel.

16. The pumping device of the micro channel of claim 14, wherein the additional pumping unit is configured to push a piston into at least one of the valve body cavities, so that the sealing film seals the at least one of the valve body cavities to close a corresponding liquid channel, and is further configured to push the piston to leave the at least one of the valve body cavities, so that the sealing film releases the at least one of the valve body cavities to open the corresponding liquid channel.

17. The pumping device of the micro channel of claim 1, wherein the downstream functional device includes at least one of a cell filtration device, a gas exchange device, or a dialysis device.

18. The pumping device of the micro channel of claim 17, wherein the cell filtration device includes a hollow fiber column.

19. The pumping device of the micro channel of claim 1, wherein the first liquid cavity and the second liquid cavity are configured such that when the third valve is opened and the first valve is closed, a gas is suctioned out from the first liquid cavity, and the liquid in the bioreactor is suctioned into the first liquid cavity through the third liquid channel, the fourth valve is closed, the second valve is opened, and the gas is pushed into the second liquid cavity, the liquid in the second liquid cavity leaves the second liquid cavity and is pushed to the downstream functional device through the second liquid channel.

20. The pumping device of the micro channel of claim 1, wherein the first liquid cavity and the second liquid cavity are configured such that when the third valve is closed and the first valve is opened, a gas is pushed into the first liquid cavity, and the liquid in the first liquid cavity leaves the first liquid cavity and is pushed into the downstream functional device through the first liquid channel, the fourth valve is opened, the second valve is closed, the gas is suctioned out from the second liquid cavity, and the liquid in the bioreactor is suctioned into the second liquid cavity through the fourth liquid channel.

* * * * *